United States Patent [19] [11] 4,169,098
Hellmer et al. [45] Sep. 25, 1979

[54] PROCESS FOR UTILIZATION OF THE REACTION HEAT GENERATED BY THE CATALYTIC OXIDATION OF O-XYLENE

[75] Inventors: Lars Hellmer, Widdersdorf; Gerhard Keunecke, Geyen, both of Fed. Rep. of Germany

[73] Assignee: Davy Powergas GmbH, Cologne, Fed. Rep. of Germany

[21] Appl. No.: 760,972

[22] Filed: Jan. 21, 1977

[30] Foreign Application Priority Data

Jan. 27, 1976 [DE] Fed. Rep. of Germany ....... 2602895

[51] Int. Cl.$^2$ ............................................. C07D 307/89
[52] U.S. Cl. .................................................. 260/346.4
[58] Field of Search ...................................... 260/346.4

[56] References Cited

U.S. PATENT DOCUMENTS

| 3,248,453 | 4/1966 | Beyrard | 260/346.4 X |
| 3,535,345 | 10/1970 | Egbert | 260/346.4 |
| 4,119,645 | 10/1978 | Awroy et al. | 260/346.4 |

OTHER PUBLICATIONS

Zimmer, Chemical Engineering, 3-4-74, pp. 82 and 83.
Zimmer, Hydrocarbon Processing, 2-1974.
Informations-Chimie Special French Processes, 12-1973.

Primary Examiner—Richard Raymond
Attorney, Agent, or Firm—Bernard & Brown

[57] ABSTRACT

A process for utilization of the reaction heat generated by the catalytic oxidation of o-xylene with air to phthalic anhydride in a tubular reactor, which heat is partially carried away from the reactor by the reaction gas and partially by fused salt used as a cooling medium. Water is heated by heat exchange with the hot reaction gas, evaporated by heat exchange with the fused salt and the steam is superheated and expanded in a condensation turbine coupled with the feed air compressor. The hot reaction gas is used successively to heat, or evaporate, a heat carrier liquid serving for the heating of the phthalic anhydride distillation, and the pressurized water. Low pressure steam can be generated by heat exchange of pressurized water with the reaction gas and used for heating the feed air and/or o-xylene. Preferably, the evaporation and superheating of the heated pressure water is effected in two fused salt cooling stages; the compressed air is successively heated by heat exchange with low pressure steam generated by cooling of the reaction gas and with the high pressure steam generated by cooling of the fused salt; and, the heating liquid and the pressurized water are heated in a two-stage heat exchanger.

14 Claims, 1 Drawing Figure

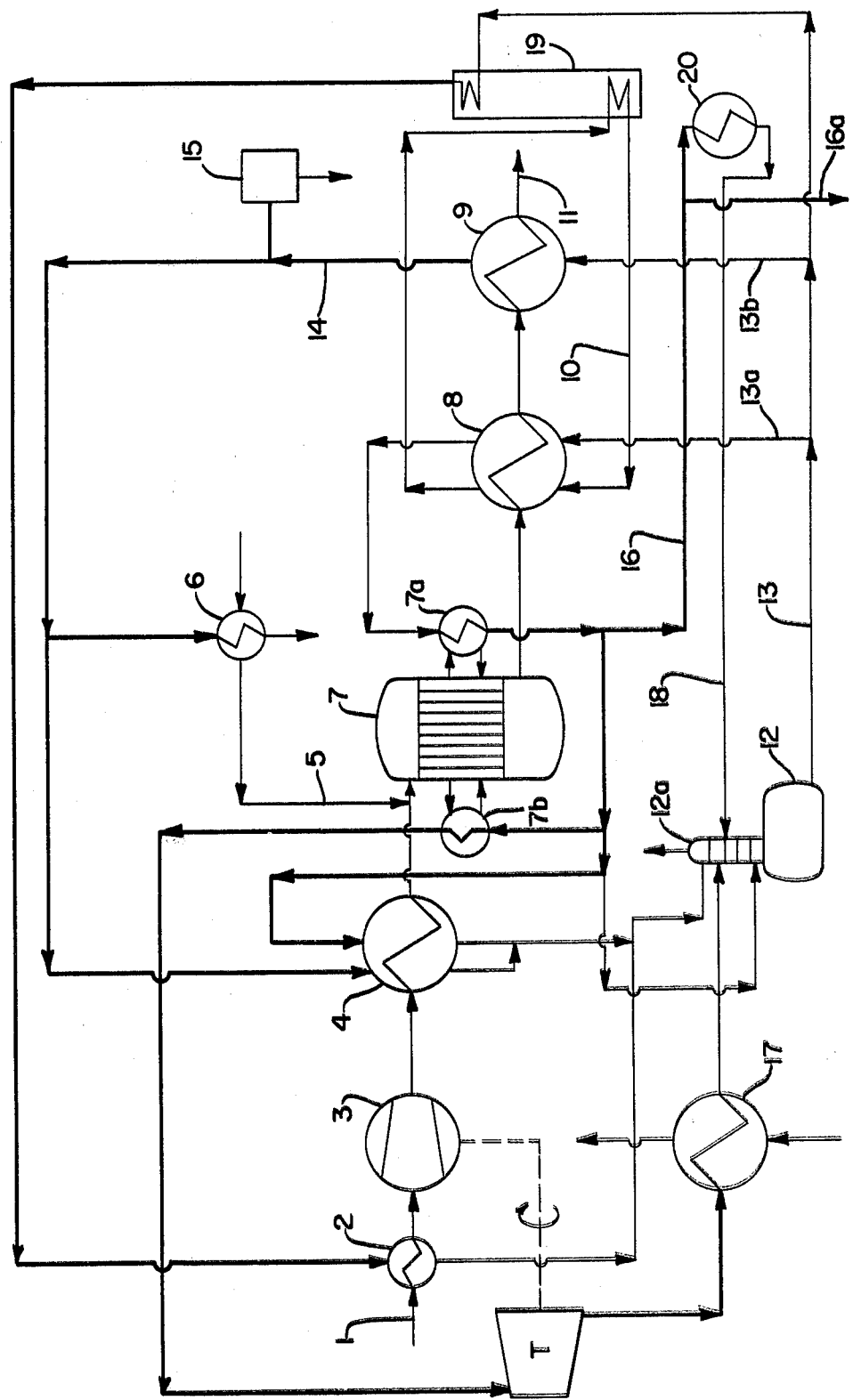

PROCESS FOR UTILIZATION OF THE REACTION HEAT GENERATED BY THE CATALYTIC OXIDATION OF O-XYLENE

This invention relates to a process for utilization of the reaction heat generated by the catalytic oxidation of o-xylene with air to phthalic anhydride in a tubular reactor, which heat is carried away from the reactor partially by the reaction gas and partially by a salt melt used as a cooling medium.

BACKGROUND OF THE INVENTION

High-temperature air oxidation of o-xylene, or naphthalene, over a catalyst such as a molybdenum or vanadium oxide, to produce phthalic anhydride is well-known. Reaction temperatures of 350° to 475° C. with contact times of a half-second to several seconds can be used. Cooling of the reactors is usually carried out by circulating a molten salt. Reactor capacity in this process is, however, typically relatively low because of limitations of the heat removal system in maintaining constant temperature. The reactor effluent is treated to separate the phthalic vapors and the recovered phthalic anhydride is purified. The purification typically is carried out by distillation.

When oxidizing o-xylene to phthalic anhydride a heat amount of 264.8 kcal/mol is released which must be removed in order to control the reaction. Therefore, a tubular reactor is used and is cooled by a fused salt bath, typically consisting of $KNO_3$ and $NaNO_2$, which circulates around the reactor tubes. The salt bath is then cooled by heat exchange with evaporating water. One part of the reaction heat is carried away via the circulating fused salt as steam, whereas another part leaves the reactor with the exiting hot reaction gas stream containing phthalic vapors. It is known to utilize the heat transferred to the fused salt bath and the heat carried away by the reaction gas stream for steam production and to use this steam for various heat requirements within the plant and/or to transfer it to a steam supply network for other purposes. From "Hydrocarbon Processing" 53 (February, 1974), pp. 111–112, it is known, for example, to heat water by heat exchange with the hot reaction gas, then to evaporate it in the salt bath cooler, superheat this steam in the reaction gas cooler, and use this superheated steam for the drive of the air compressor. In this method, the compressor is apparently driven by a back pressure turbine, because substantial amounts of back pressure steam at 11 atm. abs. are available. In this operation, a heating or evaporation of a heat carrier suitable for the heating of distillation columns is not provided, and the temperature of the available back pressure steam is not sufficient for the heating of the distillation unit. Using the ordinary organic heat carrier liquids for heating of the distillation unit by heat exchange with the fused salt bath is not desirable for reasons of safety because of the strongly oxidizing effect of this fused salt mixture. A further disadvantage of the known method is that the surplus steam is delivered at a comparatively low pressure.

An object of the present invention is to provide a process for the efficient utilization of the reaction heat generated by the catalytic oxidation of o-xylene with air to phthalic anhydride in a tubular reactor, in which process, in addition to the drive energy for the air compressor and the amounts of heat necessary in the plant, also the heat requirements for the heat carrier liquid needed for heating purposes in the distillation unit of the anhydride recovery stage of the process are provided. Another object of the present invention is to provide a process for the efficient utilization of the reaction heat generated by the catalytic oxidation of o-xylene with air to phthalic anhydride in a tubular reactor in which process surplus steam is to be delivered at a higher pressure and a higher temperature than is possible by the back pressure of a back pressure turbine.

DESCRIPTION OF THE INVENTION

According to this invention, these problems are solved by (a) successively heating, or evaporating, a heat carrier liquid serving for the heating of the phthalic anhydride distillation, heating pressurized water and then evaporating further pressurized water by heat exchange with the hot reaction gas, (b) evaporating and superheating the heated pressurized water by heat exchange with the fused salt and (c) expanding the superheated steam in a condensation turbine coupled with the air compressor. The reaction gas leaving the reactor is accordingly cooled in three series-connected stages with the heat carrier liquid circulating between the distillation part and the reaction part of the plant and the reaction gas first of all coming into heat exchange with said heat carrier liquid so that its temperature can be increased to the necessary high level, e.g., about 280° to 320° C. In this way, safety risks are avoided, which would exist in case of a heat exchange between the organic heat carrier liquid, e.g., a mixture of Diphenyl and Diphenyloxide, and the fused salt which has a strong oxidizing effect. The reaction gas, partially cooled down by this heat exchange, then serves for heating the pressurized water from which high pressure steam is subsequently produced for the turbine drive and for reheating the heat carrier liquid used for the phthalic anhydride separators and from which water, if necessary, surplus steam is produced which can be delivered to the plant. Since the steam amounts required for re-heating the heat carrier liquid for the separators fluctuate periodically, and the steam production is constant in time, correspondingly fluctuating surplus steam amounts are withdrawn to the plant. Finally, the process of the invention has the advantage that the heat exchange is effected in said exchange stages between a gas phase and a possibly boiling liquid phase resulting in a comparatively good heat transfer and in heat exchange areas which are not uneconomically large. Suitably, water at a pressure in the range from about 20 to 75 atm. abs. is heated by the reaction gas and water at a pressure in the range from about 4 to 10 atm. abs. is evaporated by said reaction gas.

Preferably the low pressure steam produced by heat exchange with the reaction gas is at least partially used for the heating of the feed air and/or o-xylene. Moreover, this steam can be used for heating the plant. The produced low pressure steam is completely consumed in the plant so that surplus steam is only delivered at high pressure. The low pressure steam generated in the distillation unit is suitably also used for preheating the oxidation air. Furthermore, it is provided that the pressurized water used for the production of high pressure steam is heated by the reaction gas to a temperature within the range from about 220° to 260° C., preferably to a temperature within the range from about 235° to 245° C. The heating temperature depends on the temperature in the condensate collector, as well as on how far the reaction gas has already been cooled down by the previous heat exchange with the heat carrier liquid. The feed water from the condensate collector can be available at a temperature in the range from, e.g., about 105° to 145° C., and the reaction gas, leaving the reactor at about 380° C., can have been cooled down to a temperature within the range from, e.g., about 305° to 310° C. by heat exchange with the heat carrier liquid.

Suitably, the pressure water is evaporated and superheated in two fused salt cooling stages. In the first fused salt cooling stage, the pressurized water is evaporated; in the second fused salt cooling stage the steam is merely superheated. Two separate heat exchangers can be used as the fused salt cooling stages. The amounts of fused salt circulating through them can be same or different. The steam for heating the heat carrier liquid for the separators as well as surplus steam can be withdrawn from the steam line connecting both the fused salt cooling stages. Suitably, the steam is superheated to a temperature in the range from about 275° to 330° C., preferably from about 275° to 290° C. The steam superheated in this way is then expanded in the condensation turbine, which drives the air compressor. Of course, it is always possible to deliver superheated steam as surplus steam.

Preferably, prior to the loading with o-xylene, the compressed air is successively heated by heat exchange (a) with the low pressure steam generated by the reaction gas cooling and (b) with the high pressure steam generated by fused salt cooling. This heat exchange can be effected in a two-stage heat exchanger. In this way, the steam is condensed; the condensate flows into the condensate collector; and, the air temperature is increased, for example, to about 135° to 160° C.

According to an embodiment of the invention, the heat carrier liquid and the pressurized water are heated in a two-stage heat exchanger, whereas the pressurized water is evaporated in a separate second heat exchanger for the purpose of generating low pressure steam.

The process of this invention is especially suitable for the catalytic oxidation of o-xylene with air within the explosion range, i.e., with o-xylene concentrations of more than 1.0% by vol., particularly with o-xylene concentrations in the range from 1.0 to 1.7% by vol., because an increased part of the reaction heat can be used within the plant or can be delivered as surplus steam due to the smaller throughput of reaction gas volume compared with an oxidation below the explosion range. However, the process is not limited to an operation in the explosion range but can also be applied with similar advantages when using lower o-xylene concentrations.

BRIEF DESCRIPTION OF THE DRAWING

The invention is illustrated herebelow in connection with the drawing which shows the heat flow diagram of a plant for the production of phthalic anhydride with utilization of the reaction heat according to the invention.

DETAILED DESCRIPTION OF THE DRAWING

The air required for the oxidation is sucked in at 1, heated in the heat exchanger 2 by low pressure steam derived from the distillation unit 19, compressed in the air compressor 3, and further heated in the heat exchanger 4 in two stages by low pressure steam and subsequently by high pressure steam, e.g., to a temperature of about 150° C. Liquid o-xylene fed via line 5 is injected into the hot air stream, the o-xylene having been heated to about 140° C. by low pressure steam in the heat exchanger 6. The air, loaded with o-xylene, enters the tubular reactor 7 at about 135° C. The gas mixture flows through the tubes filled with catalyst while being oxidized. A salt melt circulating around the reactor tubes, absorbs a part of the oxidation heat, flows to two external heat exchangers 7a and 7b and is cooled by evaporating water and/or steam in these heat exchangers.

The reaction gas leaving the reactor 7 flows through a two-stage heat exchanger 8 in the first stage of which a liquid heat carrier is heated, or evaporated, which circulates through line 10 and is used for heating the distillation columns 19 for the purification of the phthalic anhydride. In the second stage of the heat exchanger 8 pressurized water is heated which is expanded in the turbine T after being evaporated in the fused salt cooler 7a and superheated in the fused salt cooler 7b. After leaving the heat exchanger 8, the reaction gas flows through another heat exchanger 9 in which low pressure steam is generated by evaporation of pressurized water. The reaction gas cooled in the exchangers 8 and 9 then flows through line 11 to the phthalic anhydride separators (not shown).

The various condensates are collected in the reservoir 12 equipped with a deaerator 12a, a suitable water temperature, e.g., about 130° C., being maintained in the reservoir. The water in the line 13 is pressurized by pumps (not shown) and flows at this pressure via lines 13a and 13b to the heat exchangers 8 and 9, respectively, and the distillation columns 19. The low pressure steam from the heat exchanger 9 is passed via line 14 to the heat exchangers 4 and 6 for the preheating of air and o-xylene, respectively, as well as to further heat-consumers 15 within the plant. Only a part of the high pressure steam generated in the fused salt cooler 7a is superheated in the fused salt cooler 7b. Another part is used for preheating the compressed air in the heat exchanger 4; a further part is passed via line 16 to the oil heater 20 in which the liquid heat carrier medium required for melting down the phthalic anhydride from the separators is heated. The surplus steam is delivered at 16a to the high pressure steam supply network of the factory.

The steam superheated in the fused salt cooler 7b is expanded in the turbine T coupled with the air compressor 3, to the condensation pressure of the condenser 17 arranged downstream of the turbine and charged with cooling water. The condensates from condenser 17 and the heat exchangers 2, 4, 6 and 7a, as well as the condensates from the oil heater 20 brought up via line 18 are passed to the deaerator 12a and are then recirculated starting from the reservoir 12.

EXAMPLE

In a plant with the utilization of the reaction heat as shown in the drawing, 180,000 Nm$^3$/h air are sucked in and, after being compressed to 1.65 atm. abs. in compressor 3 and heated to 150° C. in exchanger 4, they are loaded with 10,800 kg/h o-xylene. At a temperature of 135° C., the mixture enters the reactor 7; the reaction gas leaves it at about 375° C. The reaction gas heats 355 t/h organic heating liquid from 290° to 310° C. and 57.5 t/h water at a pressure of 50 atm. abs. from 140° to 240° C. in exchanger 8 and finally it evaporates 4.2 t/h water at 7 atm. abs. in exchanger 9.

The reaction gas is cooled down in the three heat exchanger stages to 308° C. and 208° C. in exchanger 8 and 170° C. in exchanger 9, respectively. The hot pressure water from exchanger 8, having a temperature of 240° C., is evaporated in the fused salt cooler 7a while absorbing $23.9 \cdot 10^6$ kcal/h. Of this steam 27 t/h are heated to 280° C. in the fused salt cooler 7b while absorbing $0.43 \cdot 10^6$ kcal/h.

The superheated steam generates 3800 kW in the condensation turbine T for the drive of the air compressor 3. Moreover, 7.7 t/h of the high pressure steam from the fused salt cooler 7a are available to be used for the air preheater 4, and, on the average, 3.3 t/h of the pressure steam are available to be used for the oil heater 20. On the average, 11 t/h surplus steam are delivered at 263° C. and 50 atm. abs. via line 16a. 4.2 t/h low pressure steam are produced in the heat exchanger 9 covering the required heat of the heat-consumers 4 partially, as well as of the heat-consumers 6 and 15.

It is claimed:

1. In a process for the utilization of the reaction heat generated by the catalytic oxidation of o-xylene with pressurized air to produce phthalic anhydride in a tubular reactor, which heat is partially carried away from the reactor by the reaction gas and partially by fused salt used as a cooling medium, water being heated by heat exchange with the hot reaction gas and being evaporated by heat exchange with the fused salt, the steam being superheated and used for the drive of a feed air compressor, the phthalic anhydride being separated from the reaction gas and purified by distillation, the improvement which comprises utilizing the heat in said reaction gas by successively (a) heating, or evaporating, a heat carrier liquid by heat exchange with said reaction gas, said liquid being used to heat the phthalic anhydride distillation, (b) heating pressurized water by heat exchange with said reaction gas and then (c) evaporating pressurized water by heat exchange with said reaction gas to produce relatively low pressure steam; evaporating and superheating the heated pressurized water by heat exchange with said fused salt to produce superheated relatively high pressure steam; and expanding said superheated steam in a condensation turbine coupled with said air compressor.

2. The process according to claim 1, characterized in that water at a pressure of 20 to 75 atm. abs. is heated by the reaction gas and water at a pressure of 4 to 10 atm. abs. is evaporated by the reaction gas.

3. The process according to claim 2, characterized in that the steam is superheated to a temperature in the range from 275° to 330° C.

4. The process according to claim 3, characterized in that the pressurized water is heated to a temperature in the range from 220° to 260° C. by the reaction gas.

5. The process according to claim 1, characterized in that the low pressure steam generated by heat exchange with the reaction gas is at least partially used for heating at least one of said air and o-xylene.

6. The process according to claim 1, characterized in that the evaporation and superheating of the heated pressure water is effected in two fused salt cooling stages.

7. The process according to claim 1, characterized in that the compressed air is successively heated by heat exchange with said low pressure steam generated by cooling of the reaction gas and with said high pressure steam generated by cooling of the fused salt.

8. The process according to claim 1, characterized in that the heating liquid and the pressurized water are heated in a two-stage heat exchanger.

9. The process according to claim 4, characterized in that the low pressure steam generated by heat exchange with the reaction gas is at least partially used for heating at least one of said air and o-xylene.

10. The process according to claim 9, characterized in that the evaporation and superheating of the heated pressure water is effected in two fused salt cooling stages.

11. The process according to claim 10, characterized in that the compressed air is successively heated by heat exchange with said low pressure steam generated by cooling of the reaction gas and with said high pressure steam generated by cooling of the fused salt.

12. The process according to claim 11, characterized in that the heating liquid and the pressurized water are heated in a two-stage heat exchanger.

13. The process according to claim 6, characterized in that the low pressure steam generated by heat exchange with the reaction gas is at least partially used for heating at least one of said air and o-xylene.

14. The process according to claim 13, characterized in that the compressed air is successively heated by heat exchange with said low pressure steam generated by cooling of the reaction gas and with said high pressure steam generated by cooling of the fused salt.

* * * * *